US005830692A

United States Patent [19]
Böck et al.

[11] Patent Number: 5,830,692
[45] Date of Patent: Nov. 3, 1998

[54] EXPRESSION SYSTEM WHICH CAN BE REGULATED

[75] Inventors: August Böck, Geltendorf; Dagmar Mayer, München; Verena Schlensog, Ismaning; Anton Candussio, München, all of Germany

[73] Assignee: Consortium für Elektrochemische Industrie GmbH, Munich, Germany

[21] Appl. No.: 614,686

[22] Filed: Mar. 12, 1996

[30] Foreign Application Priority Data

Mar. 24, 1995 [DE] Germany .................. 195 10 930.9
Apr. 13, 1995 [DE] Germany .................. 195 14 056.7

[51] Int. Cl.$^6$ ................... C12P 21/02; C07H 21/04; C12N 1/21; C12N 15/74
[52] U.S. Cl. ............... 435/691; 435/252.3; 435/252.33; 435/320.1; 536/23.1; 536/24.1
[58] Field of Search ............... 435/320.1, 69.1, 435/252.3, 252.33; 536/23.1, 24.1

[56] References Cited

FOREIGN PATENT DOCUMENTS 0338410  9/1994  European Pat. Off. .
3926076  10/1990  Germany .

OTHER PUBLICATIONS

Journal of Bacteriology, Mar. 1993, pp. 1392–1404, K. Blomqvist et al., Characterizaton of the Genes of the 2,3–Butanediol Operons from *Klebsiella terrigena* and *Enterobacter aerogenes* is an English reference.
Gene 53 (1987), pp. 85–96, Elsevier, GEN 01960, R.W. Simons et al., "Improved single and multicopy lac–based cloning vectors for protein and operon fusions" is an English reference.
Proc. Natl. Acad. Sci. USA, vol. 76, No. 9, pp. 4530–4533, Sep. 1979, Genetics, Malcolm J. Casadaban and Stanley N. Cohen, "Lactose genes fused to exogenous promoters in one step using a Mu–lac bacteriophage: In vivo probe for transcriptional control sequences" is an English language reference.
Gene 48, (1986), pp. 119–131, Elsevier, GEN 01797, Jens P. Fürste et al., "Molecular cloning of the plasmid RP4 primase region in a multi–host–range tacP expression vector" is an English language reference.
Journal of Bacteriology, Jun. 1992, pp. 3474–3478, vol. 174, No. 11, G. Sawers and Bernhard Suppmann, "Anaerobic Induction of Pyruvate Formate–Lyase Gene Expression is Mediated by the ArcA and FNR Proteins" is an English language reference.
Applied and Environmental Microbiology, Dec. 1976, pp. 781–791, vol. 32, No. 6, William E. Balch and R.S. Wolfe "New Approach to the Cultivation of Methanogenic Bacteria: 2–Mercaptoethanesulfonic Acid (HS–CoM)–Dependent Growth of *Methanobacterium ruminantium* in a Pressurized Atmosphere" is an English language reference.

Genetics 90: 427–461 Nov. 1978, Nancy Kleckner et al., "Properties of the Translocatable Tetracycline–Resistance Element Tn10 in *Escherichia Coli* and *Bacteriophage Lambda*" is an English language reference.
John Wiley & Sons, New York 1987 by Current Protocols in Molecular Biology, F. M. Ausubel et al. "Preparation of Genomic DNA from Bacteria" is an English language reference.
Analytical Biochemistry 114, pp. 193–197 (1981), David S. Holmes and Michael Quigley, "A rapid method for the preparation of bacterial plasmids" is an English language reference.
Cold Spring Harbor Laboratory 1982, Molecular Cloning, A Laboratory Manual, T. Maniatis et al. "Transformation of *Escherichia coli* by Plasmid DNA" is an English language reference.
Cold Spring Harbor Laboratory 1972, pp. 352–355, Experiments in Molecular Genetics, Jeffrey H. Miller, Experiment 48, "Assay of β–Galactosidase"is an English language reference.
Cold Spring Harbor Laboratory 1972, pp. 121–124, Experiments in Molecular Genetics, Jeffrey H. Miller, Experiment 13, "Ultraviolet Light Mutagenesis" is an English language reference.
Cold Spring Harbor Laboratory 1972, pp. 125–129, Experiments in Molecular Genetics, Jeffrey H. Miller, Experiment 14, "Nitrosoguanidine Mutagenesis" is an English language reference.
Cold Spring Harbor Laboratory 1982, pp. 98–148, Molecular Cloning, A Laboratory Manual, T. Maniatis et al. "Enzymes Used in Molecular Cloning" is an English language reference.
Gene, 33 (1985), pp. 103–119, Elsevier, Gene 1167, Celeste Yanisch–Perron et al., "Improved M13 phage cloning vectors and host strains: nucleotide sequences of the M13mp18 and pUC19 vectors" is an English language reference.
Department of Microbiology, University of Washington, Seattle, Wash. 98195 (US), 1977, F. Bolivar et al., "Construction and Characterization of new Cloning Vehicles" is an English language reference.
Gene 47 (1986), pp. 269–277, Elsevier, GEN 01776, Florian Binder et al. "Cyclodextrin–glycosyltransferase from *Klebsiella pneumoniae* M5a1: cloning, nucleotide sequence and expression" is an English language reference.

(List continued on next page.)

*Primary Examiner*—Nancy Degen
*Attorney, Agent, or Firm*—Collard & Roe, P.C.

[57] ABSTRACT

An expression system can be regulated by acetate, pH and oxygen, which expression system includes a trans-acting regulator protein and a promoter which can be activated by this protein. Any desired structural genes are maximally expressed under the control of the expression system at an oxygen partial pressure, $pO_2$, of 0–5% and a pH of 6.0–6.5, and in the presence of acetate at a concentration of 40–60 mM. There is also a process for preparing this expression system, and a process for using this expression system.

12 Claims, 10 Drawing Sheets

OTHER PUBLICATIONS

Proc. Natl. Acad. Sci. USA, vol. 74, No. 12, pp. 5463–5467, Dec. 1977, Biochemistry, F. Sanger et al., "DNA sequencing with chain–terminating inhibitors" is an English language reference.

Analytical Biochemistry 170, 38–44, (1988), Stefan Fiedler and Reinhard Wirth "Transformation of Bacteria with Plasmid DNA by Electroporation" is an English language reference.

Analytical Biochemistry 200, 81–88 (1992), Win Ping Deng and Jac A. Nickoloff, "Site–Directed Mutagenesis of Virtually Any Plasmid by Eliminating a Unique Site" is an English language reference.

Eur. J. Biochem. 191, 177–185 (1990), FEBS 1990, Anton Candussio et al., "Biochemical and genetic analysis of a maltopentaose–producing amylase from an alkaliphilic bacterium" is an English language reference.

FEMS Microbiology Letters 2 (1977), 47–50, Elsevier, Yvonne A. Begg et al., "The identification of mutants of *Escherichia Coli* deficient in formate dehydrogenase and nitrate reductase activities using dye indicator plates" is an English language reference.

Gene, 28 (1984), 351–359, Elsevier, Gene 1007, Steven Henikoff, "Undirectional digestion with exonculease III creates targeted breakpoints for DNA sequencing" is an English language reference.

Journal of Bacteriology, vol. 177, No. 18, 1995, pp. 5262–5269 D. Mayer et al. "Identification of the Transcriptional Activator Controlling the Butanediol Fermentation Pathway in *Klebsiella terringena*".

Journal of Bacteriology, vol. 175, No. 5, 1993, pp. 1392–1404 K. Blomquist et al. "Characterization of the Genes of the 2,3–Butanediol Operons from *Klebsiella terrigena* and *Enterobacter aerogenes*".

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 290 amino acids
        ( B ) TYPE: amino acid
        ( C ) STRANDEDNESS: double
        ( D ) TOPOLOGY: linear ( i i ) MOLECULE TYPE: protein ( v i i ) ORIGINAL SOURCE:
        ( A ) ORGANISM:Klebsiella terrigena
        ( B ) STRAIN:DSM2867

( x i ) SEQUENCE DESCRIPTION: SEQ ID NO: 1:

```
Met  Glu  Leu  Arg  Tyr  Leu  Arg  Tyr  Phe  Val  Ala  Val  Ala  Glu  Ala  Arg
  1              5                        10                       15

Asn  Phe  Thr  Arg  Ala  Ala  His  Asp  Leu  Gly  Ile  Ser  Gln  Pro  Pro  Leu
               20                        25                       30

Ser  Gln  Gln  Ile  Gln  Arg  Leu  Glu  Arg  Glu  Ile  Gly  Thr  Pro  Leu  Leu
          35                        40                       45

Arg  Arg  Leu  Thr  Arg  Gly  Val  Glu  Leu  Thr  Glu  Ala  Gly  Glu  Ser  Phe
     50                        55                       60

Tyr  Val  Asp  Ala  Cys  Gln  Ile  Leu  Ala  Leu  Ser  Asp  Ala  Ala  Leu  Glu
 65                        70                       75                       80

Lys  Thr  Lys  Gly  Ile  Ala  Arg  Gly  Met  Asn  Gly  Ser  Leu  Val  Pro  Gly
                    85                        90                       95
```

```
Ile  Thr  Ser  Ser  Ala  Ala  Phe  His  Ser  Gln  Ile  Phe  Ser  Leu  Leu  Tyr
               100                      105                      110

Gln  Phe  Gln  Gln  Arg  Tyr  Pro  Ala  Val  Ala  Leu  Arg  Gln  Val  Glu  Gly
          115                      120                      125

Asn  Met  Ala  Thr  Leu  Met  His  Ala  Leu  Gly  Glu  Ala  Glu  Leu  Asp  Ile
     130                      135                      140

Ala  Phe  Val  Arg  Leu  Pro  Cys  Glu  Ser  Ser  Lys  Ala  Phe  Asn  Leu  Arg
145                      150                      155                      160

Ile  Ile  Ala  Glu  Glu  Pro  Met  Val  Ile  Ala  Leu  His  Arg  Ser  His  Pro
               165                      170                      175

Leu  Ser  Gly  Glu  Ser  Ala  Leu  Ser  Leu  Ala  Gln  Leu  Ser  Asp  Ala  Val
               180                      185                      190

Pro  Val  Ile  Phe  Pro  Pro  Glu  Val  Ala  Pro  Gly  Leu  Tyr  Glu  Gln  Val
          195                      200                      205

Tyr  Asp  Gly  Cys  Arg  Arg  Ala  Gly  Val  Asp  Met  Ser  Arg  Ala  Arg  Gln
     210                      215                      220

Ser  Ser  Gln  Ile  Ser  Ser  Ser  Ile  Ser  Met  Val  Asp  Ala  Gly  Phe  Gly
225                      230                      235                      240

Phe  Ala  Leu  Val  Pro  Gln  Ser  Met  Thr  Cys  Ile  Cys  Leu  Pro  Asn  Val
               245                      250                      255

Thr  Trp  His  Pro  Leu  Gln  Asp  Ala  Ser  Leu  Lys  Thr  Glu  Ile  Ala  Ile
               260                      265                      270

Ala  Trp  Arg  Arg  Phe  Glu  Arg  Ser  Arg  Thr  Val  Lys  Arg  Phe  Leu  Glu
               275                      280                      285

Met  Phe
     290
```

( 2 ) INFORMATION FOR SEQ ID NO:2:

( i ) SEQUENCE CHARACTERISTICS:
        ( A ) LENGTH: 1453 base pairs
        ( B ) TYPE: nucleotide
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM:Klebsiella terrigena
        ( B ) STRAIN:DSM2867

( v i i ) IMMEDIATE SOURCE:
        ( B ) CLONE: pBAK14/16

( v i i i ) POSITION IN GENOME:
        ( C ) UNITS: bp ( x i ) SEQUENCE DESCRIPTION: SEQ ID NO: 2:

```
GGATCCGCCC  GGGCTTTACG  CGCGCTGCCG  TCAGCGCGCA  GCTGGTAGAC  CTCGCTGCTA      60

AAGGCAATCA  GTTCGCCATC  GAGTTCGTTA  AAGGTGCCGA  GACCGAAGTC  GCCGTGGGTC     120

AGCAGGTCGG  CGATGGTGGT  GCTACCCTCA  TAGACCCCGC  TCAGCAGCGC  GCTCATCAGA     180

GAGGTCTGAT  AGATAACGCT  ATCAGGGTGG  TGGGCGGAGA  AGCCGCGTAC  GGTTTCGCAC     240

AGGCTCTCCT  GGCAGGTGCA  TTCAGGATAA  TGATTCACAA  TCCACTTCCT  CGTTCAACAA     300

ATATAAGAAA  GATTAAATAA  ATATTGACCC  GATTCAGCTC  TCAGTTCCAA  TATAGAATCC     360

ATGCTGGTTT  GAGACGTTTA  CGATATGGAA  CTTCGCTATT  TACGTTATTT  TGTCGCCGTT     420

GCCGAGGCGC  GGAACTTCAC  CCGGGCGGCC  CACGATCTTG  GCATTTCTCA  ACCGCCACTA     480

AGTCAGCAAA  TTCAGCGACT  TGAGCGAGAA  ATAGGGACTC  CGCTGCTGCG  TCGTTTGACG     540
```

```
CGGGGGGTTG  AGCTGACGGA  GGCCGGAGAG  TCGTTCTACG  TCGACGCGTG  TCAGATCCTC    600
GCCTTAAGCG  ATGCGGCGCT  GGAAAAAACC  AAGGGGATTG  CGCGGGGCAT  GAACGGTAGC    660
CTGGTGCCGG  GGATCACCAG  TTCAGCTGCT  TTTCATTCGC  AGATTTCTC   TTTGCTGTAC    720
CAGTTTCAGC  AGCGCTATCC  GGCGGTGGCT  CTGCGCCAGG  TCGAAGGCAA  TATGGCGACG    780
CTGATGCATG  CCCTGGGCGA  GGCGGAGCTG  GATATCGCCT  TTGTGCGCCT  GCCGTGTGAA    840
AGCAGCAAGG  CGTTTAATTT  GCGCATTATT  GCCGAGGAGC  CGATGGTTAT  CGCGCTGCAT    900
CGCTCGCACC  CGCTCTCCGG  GGAAAGTGCG  CTCTCTCTGG  CGCAGCTGAG  CGACGCGGTG    960
CCGGTTATTT  TCCCGCCGGA  GGTGGCGCCG  GGCCTCTACG  AGCAGGTTTA  TGATGGCTGT   1020
CGGCGTGCCG  GGGTCGATAT  GAGCCGCGCC  AGGCAATCTT  CACAGATCTC  GTCTTCTATT   1080
AGCATGGTGG  ACGCGGGCTT  CGGCTTTGCG  CTGGTGCCTC  AGTCGATGAC  CTGTATCTGC   1140
CTTCCCAACG  TCACATGGCA  TCCCTTGCAG  GACGCGTCGC  TGAAGACGGA  GATCGCCATC   1200
GCGTGGCGGC  GTTTTGAACG  TTCGCGGACG  GTAAAGCGTT  TTCTGGAGAT  GTTTTAGGCG   1260
GGGCGCAGGG  CTAGCAGGTA  TAGACGTTTG  CCGCGGTTGG  CCCGCGCAGG  CCGTTAACCC   1320
GACGAAACTC  AACGGAATAC  CGGGCGTCAT  CGCCGTGGAC  TCGTTGGGGG  ATAATGCGGA   1380
AATATGAACC  TGAACGTCTT  TACGACCGTC  GGAAGGGACG  ATAAGGCCTC  TGCCGGTTTT   1440
ATTATCAAAG  CTT                                                          1453
```

( 2 ) INFORMATION FOR SEQ ID NO:3:

( i ) SEQUENCE CHARACTERISTICS:
        ( A ) LENGTH: 39 base pairs
        ( B ) TYPE: nucleotide
        ( C ) STRANDEDNESS: double
        ( D ) TOPOLOGY: linear ( i i ) MOLECULE TYPE: genomic DNA ( v i i ) IMMEDIATE SOURCE:
        ( B ) CLONE: pBTL142 and pRBL2

( v i i i ) POSITION IN GENOME:
        ( C ) UNITS: bp ( x i ) SEQUENCE DESCRIPTION: SEQ ID NO: 3:

```
TATCCTGAAT  GCACCTGCCA  GGATCCCGTC  GTATTACAA                              39
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: double
        ( D ) TOPOLOGY: linear ( i i ) MOLECULE TYPE: peptide ( v ) FRAGMENT TYPE: internal fragment ( v i i ) IMMEDIATE SOURCE:
        ( B ) CLONE: pBTL142 and pRBL2

( x i ) SEQUENCE DESCRIPTION: SEQ ID NO: 4:

```
Tyr  Pro  Glu  Cys  Thr  Cys  Gln  Asp  Pro  Val  Val  Leu  Gln              1
                  5                        10
```

( 2 ) INFORMATION FOR SEQ ID NO:5:

( i ) SEQUENCE CHARACTERISTICS:
        ( A ) LENGTH: 29 base pairs (B) TYPE: nucleotide
(C) STRANDEDNESS: double
(D) TOPOLOGY: linear (ii) MOLECULE TYPE: genomic DNA (vii) IMMEDIATE SOURCE:
    (B) CLONE: pBUD100

(viii) POSITION IN GENOME:
    (C) UNITS: bp (xi) SEQUENCE DESCRIPTION: SEQ ID NO: 5:

CGAGGAAGTG GACCATGGAA AGAAACCGT　　　　29

(2) INFORMATION FOR SEQ ID NO:6:

(i) SEQUENCE CHARACTERISTICS:
    (A) LENGTH: 29 base pairs
    (B) TYPE: nucleotide
    (C) STRANDEDNESS: double
    (D) TOPOLOGY: linear (ii) MOLECULE TYPE: genomic DNA (vii) IMMEDIATE SOURCE:
    (B) CLONE: pBUD200

(viii) POSITION IN GENOME:
    (C) UNITS: bp (xi) SEQUENCE DESCRIPTION: SEQ ID NO: 6:

CGAGGAAGTG GATTATGAAA AGAAACCGT　　　　29

(2) INFORMATION FOR SEQ ID NO:7:

(i) SEQUENCE CHARACTERISTICS:
    (A) LENGTH: 25 base pairs
    (B) TYPE: nucleotide
    (C) STRANDEDNESS: single
    (D) TOPOLOGY: linear (ii) MOLECULE TYPE: additional nucleic acid
    (A) DESCRIPTION: synthetic DNA (vii) IMMEDIATE SOURCE:
    (B) CLONE: Oligo1

(viii) POSITION IN GENOME:
    (C) UNITS: bp (xi) SEQUENCE DESCRIPTION: SEQ ID NO: 7:

GGGGATCCTG GCAGGTGCAT TCAGG　　　　25

(2) INFORMATION FOR SEQ ID NO:8:

(i) SEQUENCE CHARACTERISTICS:
    (A) LENGTH: 25 base pairs
    (B) TYPE: nucleotide
    (C) STRANDEDNESS: single
    (D) TOPOLOGY: linear (ii) MOLECULE TYPE: additional nucleic acid
    (A) DESCRIPTION: synthetic DNA (vii) IMMEDIATE SOURCE:
    (B) CLONE: Oligo2

(viii) POSITION IN GENOME:
    (C) UNITS: bp (xi) SEQUENCE DESCRIPTION: SEQ ID NO: 8:

GGGGATCCAT CGTGGGCCGC CCGAG　　　　25

( 2 ) INFORMATION FOR SEQ ID NO:9:

( i ) SEQUENCE CHARACTERISTICS:
        ( A ) LENGTH: 33 base pairs
        ( B ) TYPE: nucleotide
        ( C ) STRANDEDNESS: single
        ( D ) TOPOLOGY: linear ( i i ) MOLECULE TYPE: additional nucleic acid
        ( A ) DESCRIPTION: synthetic DNA ( v i i ) IMMEDIATE SOURCE:
        ( B ) CLONE: Oligo3

( v i i i ) POSITION IN GENOME:
        ( C ) UNITS: bp ( x i ) SEQUENCE DESCRIPTION: SEQ ID NO: 9:

GGGGATCCCG CCTAAAACAT CTCCAGAAAA CGC        33

( 2 ) INFORMATION FOR SEQ ID NO:10:

( i ) SEQUENCE CHARACTERISTICS:
        ( A ) LENGTH: 10 base pairs
        ( B ) TYPE: nucleotide
        ( C ) STRANDEDNESS: single
        ( D ) TOPOLOGY: linear ( i i ) MOLECULE TYPE: additional nucleic acid
        ( A ) DESCRIPTION: synthetic DNA ( v i i ) IMMEDIATE SOURCE:
        ( B ) CLONE: Oligo4

( v i i i ) POSITION IN GENOME:
        ( C ) UNITS: bp ( x i ) SEQUENCE DESCRIPTION: SEQ ID NO: 10:

CGGAATTCCG        10

( 2 ) INFORMATION FOR SEQ ID NO:11:

( i ) SEQUENCE CHARACTERISTICS:
        ( A ) LENGTH: 43 base pairs
        ( B ) TYPE: nucleotide
        ( C ) STRANDEDNESS: single
        ( D ) TOPOLOGY: linear ( i i ) MOLECULE TYPE: additional nucleic acid
        ( A ) DESCRIPTION: synthetic DNA ( v i i ) IMMEDIATE SOURCE:
        ( B ) CLONE: Oligo5

( v i i i ) POSITION IN GENOME:
        ( C ) UNITS: bp ( x i ) SEQUENCE DESCRIPTION: SEQ ID NO: 11:

TCTAGAAGCT TCGCGACCAA CCGCGGCAAA CGTCTATACC TGC        43

( 2 ) INFORMATION FOR SEQ ID NO:12:

( i ) SEQUENCE CHARACTERISTICS:
        ( A ) LENGTH: 37 base pairs
        ( B ) TYPE: nucleotide
        ( C ) STRANDEDNESS: single
        ( D ) TOPOLOGY: linear ( i i ) MOLECULE TYPE: additional nucleic acid
        ( A ) DESCRIPTION: synthetic DNA ( v i i ) IMMEDIATE SOURCE:

( B ) CLONE: Oligo6

( v i i i ) POSITION IN GENOME:
( C ) UNITS: bp ( x i ) SEQUENCE DESCRIPTION: SEQ ID NO: 12:

TCTAGAAGCT TCCATGGTCC ACTTCCTCGT TCAACAA 37

( 2 ) INFORMATION FOR SEQ ID NO:13:

( i ) SEQUENCE CHARACTERISTICS:
( A ) LENGTH: 40 base pairs
( B ) TYPE: nucleotide
( C ) STRANDEDNESS: single
( D ) TOPOLOGY: linear ( i i ) MOLECULE TYPE: additional nucleic acid
( A ) DESCRIPTION: synthetic DNA ( v i i ) IMMEDIATE SOURCE:
( B ) CLONE: Oligo7

( v i i i ) POSITION IN GENOME:
( C ) UNITS: bp ( x i ) SEQUENCE DESCRIPTION: SEQ ID NO: 13:

TCTAGAAGCT TCCATGGAAA GAAACCGTTT TTTTAATACC 40

( 2 ) INFORMATION FOR SEQ ID NO:14:

( i ) SEQUENCE CHARACTERISTICS:
( A ) LENGTH: 41 base pairs
( B ) TYPE: nucleotide
( C ) STRANDEDNESS: single
( D ) TOPOLOGY: linear ( i i ) MOLECULE TYPE: additional nucleic acid
( A ) DESCRIPTION: synthetic DNA ( v i i ) IMMEDIATE SOURCE:
( B ) CLONE: Oligo8

( v i i i ) POSITION IN GENOME:
( C ) UNITS: bp ( x i ) SEQUENCE DESCRIPTION: SEQ ID NO: 14:

TCTAGAAGCT TGAATTCTTA AAACGAGCCA TTCGTTGTTT G 41

( 2 ) INFORMATION FOR SEQ ID NO:15:

( i ) SEQUENCE CHARACTERISTICS:
( A ) LENGTH: 36 base pairs
( B ) TYPE: nucleotide
( C ) STRANDEDNESS: single
( D ) TOPOLOGY: linear ( i i ) MOLECULE TYPE: additional nucleic acid
( A ) DESCRIPTION: synthetic DNA ( v i i ) IMMEDIATE SOURCE:
( B ) CLONE: Oligo9

( v i i i ) POSITION IN GENOME:
( C ) UNITS: bp ( x i ) SEQUENCE DESCRIPTION: SEQ ID NO: 15:

GAACGAGGCC GTGGATTATG AAAAGAAACC GTTTTT 36

EXPRESSION SYSTEM WHICH CAN BE REGULATED

BACKGROUND OF THE INVENTION

1. Field of the Invention

The present invention relates to an expression system which can be regulated, and to processes for preparing it and using it.

2. The Prior Art

The production of defined proteins using recombinant production systems represents an important area of application for modern genetic engineering. These recombinant production systems consist of at least two components, namely a) a host, which provides the cellular machinery for the protein production, and b) a recombinant DNA which encodes the protein which is to be produced.

Examples of known host systems are microorganisms, animals, plants or eukaryotic cell cultures. Microorganisms such as fungi or bacteria, particularly preferably E. coli, are used as host systems for producing large quantities of recombinant proteins.

The recombinant DNA, which contains the genetic information for producing a defined protein, can either be integrated into a host chromosome or be present episomally, in the form of a plasmid or cosmid, or phage or virus. In addition to the genetic information for the protein which is to be produced, the recombinant DNA contains regulatory elements, so-called promoters, which are required for the first step in the expression of structural genes, i.e. transcription of the DNA sequence into RNA. In this context, promoters, which are defined, short DNA regions, serve as recognition sites for RNA polymerases, which are enzymes which catalyze the transcription of DNA sequences into RNA.

Promoters are frequently functionally combined with DNA regions which serve as recognition sites or binding sites for a group of proteins which, depending on different stimuli, affect the activity of promoters and are therefore designated regulators. By means of these regulators binding to their binding sites, promoters which are linked to these sites can be activated (activators) or repressed (repressors). In genetic engineering or manipulation systems for producing recombinant proteins, these regulator/promoter interactions are used in order to regulate the production of target proteins.

Examples of these systems which are used industrially are the lac promoter and tac promoter, which are promoters which are inactivated by binding the so-called lac repressor protein. When lactose or lactose analogs, such as IPTG, are added, the repressor dissociates from its binding site; this results in induction of the expression of genes which are located distally to the promoter.

Another regulatory system which is used industrially consists of the combination of trp promoter and trp repressor protein. It is only in the presence of tryptophan that the repressor binds to the promoter and inactivates it.

These systems possess several disadvantages in relation to their use for the industrial production of recombinant proteins. The substances which are used to induce or repress these systems are expensive and difficult to handle, particularly when they are metabolizable substances such as lactose or tryptophan. The molar ratio of regulator protein and promoter has a powerful influence on the repressibility of the expression system. When the promoter is present in excess, such systems are not completely repressible, since the repressor is titrated out. Over and above this, the promoters which are dependent on the lac repressor cannot be induced completely when the repressor is present in molar excess.

DE 3,926,076 A1 (corresponds to CA-A-2015046) describes the use of the pfl promoter for producing recombinant proteins. In the presence of the regulator protein FNR, this E. coli—specific promoter is induced under anaerobic conditions and by pyruvate, and repressed by oxygen. In comparison to the lac promoter, tac promoter or trp promoter, the pfl promoter enjoys the advantage that it is simple and cheap to induce on an industrial scale. Regulation is effected by the activity of the promoter being suppressed at the beginning of the fermentation by the supply of oxygen. In the late phase of logarithmic growth, oxygen limitation, which can be enhanced or regulated by fermentation technology, automatically sets in as a result of the high level of cell mass. In addition, pyruvate, which enhances the expression, is formed by the host organism in this phase of growth. Where appropriate, further pyruvate can be added externally in order to increase the induction.

Despite its advantages as compared with the other promoters, this promoter is only of limited suitability for the industrial production of recombinant proteins, for the following reasons. When the pfl promoter is used, it is not possible to induce the expression of recombinant proteins in the presence of oxygen. However, it is desirable to make use of the maximum synthetic capacity of the host, which, in the case of E. coli, is available during the exponential phase of aerobic growth, for producing recombinant proteins. Although the pfl promoter cannot be induced under aerobic conditions, it does possess a basal activity in the presence of oxygen, i.e. the pfl promoter cannot be completely repressed. The minimum residual activity of the pfl promoter under aerobic conditions is 5–10% of the activity of the promoter under optimal induction conditions (anaerobic together with pyruvate). Thus, the regulatory system consisting of FNR regulator protein and pfl promoter is a system which, while it can be regulated simply and cost effectively on an industrial scale, cannot be completely repressed and cannot be induced under all growth conditions. Consequently, the pfl promoter, like all the other known promoter systems which are used industrially, is also only of limited suitability for expressing structural genes or recombinant genes.

The DNA sequence of the 2,3-butanediol operon (bud operon) from Klebsiella terrigena has been described by Blomqvist et al. (J. Bact. (1993) Vol. 175(5), pp. 1392–1404). It is known that the formation of 2,3-butanediol is induced in Klebsiella terrigena by a low pH, by the presence of acetate and when oxygen is limited. Blomqvist et al. demonstrated that the genes which encode the proteins which are required for forming the 2,3-butanediol form an operon whose transcription is induced by oxygen limitation. The reference does not contain any information regarding induction of the promoter in the presence of oxygen.

SUMMARY OF THE INVENTION

It is an object of the present invention to make available an expression system which enables expression to be regulated simply on an industrial scale under all conditions for growing the host organism.

The present invention relates to an expression system which can be regulated by acetate, pH and oxygen, which expression system comprises a trans-acting regulator protein and a promoter which can be activated by this protein, wherein the regulator protein encompasses an amino acid sequence which is at least 75% homologous with the amino acid sequence SEQ ID NO:1, and the promoter encompasses a DNA sequence which is at least 95% homologous with the bases 315 to 397 of the DNA sequence SEQ ID NO:2.

The novel expression system maximally expresses any desired structural genes under the control of the expression system at an oxygen partial pressure, $pO_2$, of 0–5% and a pH of 6.0–6.5 and in the presence of acetate at a concentration of 40–60 mM.

The novel expression system renders it possible, for the first time, to achieve regulation, which is economical and easy to implement industrially, even on a large scale, of the expression of recombinant gene products independently of the growth phase of the producer strains and the O2 content of the culture medium.

The present invention furthermore relates to a regulator protein which brings about optimal activation of the bud promoter from *Klebsiella terrigena* (DSM2687) in association with oxygen limitation and in the presence of acetate and at a pH of the culture medium of from pH 6.0 to pH 6.5.

In the sense used above, oxygen limitation is understood to mean a partial pressure, $pO_2$, of 0–5%. Under these conditions, the acetate concentration is preferably 40–60 mM.

Preferably, the novel regulator protein encompasses an amino acid sequence which is at least 75% homologous with the amino acid sequence SEQ ID NO:1.

In a particularly preferred embodiment, the amino acid sequence of the novel regulator protein encompasses the amino acid sequence SEQ ID NO:1. In that which follows, such a regulator protein is also designated BudR.

The promoter of the expression system can encompass any DNA region which, under BudR activating conditions, leads to BudR-dependent initiation of the transcription of the genes which are located immediately downstream of this region. The physiological conditions under which BudR is maximally activated include an oxygen partial pressure, $pO_2$, of 0–5%, the presence of acetate at a concentration of 40–60 mM and a pH of 6.0–6.5.

Preferably, the promoter encompasses a DNA sequence which is at least 95% homologous with the bases 315 to 456 in the DNA SEQ ID NO 2.

In a particularly preferred embodiment, the promoter encompasses the DNA SEQ ID NO:2 in the region of the bases 315 to 397. In that which follows, such a DNA region is also designated bud promoter.

The gene for the novel regulator protein can either be synthesized completely chemically or enzymically in vitro on the basis of the sequence disclosed in SEQ ID NO:1 or be isolated from a microorganism which forms 2,3-butanediol.

The novel regulator protein is preferably obtained by expressing a gene which can be obtained in this manner. The invention also relates, therefore, to genes which encode regulator proteins according to the invention.

A gene which encodes a regulator protein according to the invention is preferably cloned using a so-called reporter strain. The person skilled in the art is familiar with the construction of reporter strains for transcription activators. Such a strain contains a gene for a protein which should preferably be detected readily, which gene is under the transcriptional control of the bud promoter. An example of a reporter strain is *E. coli* BL 142 (See Examples 5 and 7).

The gene, which is known to the person skilled in the art, for a β-galactosidase on plasmid pRS552 (Simons et al. (1987), *Gene*, Vol. 53, pp. 85–96) is preferably used as the reporter gene.

In order to clone a gene which encodes a regulator protein according to the invention, a gene library from a microorganism which forms a regulator protein according to the invention is introduced into such a reporter strain. The person skilled in the art is likewise familiar with the construction of a gene library and its isolation.

The method of cloning using a reporter strain is also known to the person skilled in the art. It can be carried out, for example, in the manner described in Casadaban & Cohen (1979) *Proc. Natl. Acad. Sci. USA* Vol. 76, No. 9, pp. 4530–4533.

In order to detect clones which form the sought-after protein, those clones are isolated from the gene library in which the reporter gene is induced at pH 6.5 and in the presence of acetate. When β-galactosidase is used as the reporter gene, the indicator plates then contain the dye X-Gal, for example. Those clones which, when β-galactosidase is used as the reporter gene, turn deeply dark blue on X-Gal-containing indicator plates contain a gene for a regulator protein according to the invention.

In a preferred embodiment of the invention, the gene for the regulator protein is isolated from a gene library of microorganisms of the genera Enterobacter or Klebsiella, preferably from *Klebsiella terrigena* (obtainable commercially from the DSM-Deutsche Sammlung für Mikroorganismen und Zellkulturen GmbH [German Collection of Microorganisms and Cell Cultures], Mascheroder Weg 1b, D-38124 Braunschweig, Germany, under the designation DSM2687). *Klebsiella terrigena* has been deposited on Mar. 31, 1995, in accordance with the Budapest Treaty, at the International Depository under the given address and under the receipt number DSM 9883.

In principle, the gene for the regulator protein can be isolated from a microorganism, for example from a microorganism which forms 2,3-butanediol, in particular from a 2,3-butanediol-forming microorganism from the Enterobacteriaceae family.

Methods for preparing a promoter which is suitable for the expression system are familiar to the person skilled in the art and are not, therefore, explained in detail. One such method for preparing a DNA fragment which provides the promoter activity according to the invention is chemical or enzymic "de novo" synthesis using the sequence information given in SEQ ID NO:2.

Another method for preparing the promoter comprises modifying an arbitrary DNA fragment by means of mutagenesis methods which are known to a person skilled in the art and using the sequence information given in SEQ ID NO:2.

Another method for preparing the promoter comprises isolating the promoter from a gene library of a microorganism which forms 2,3-butanediol. 2,3-Butanediol-forming microorganisms are well known and available to the public. Examples are representatives of the genera Enterobacter, Serratia, Erwinia, and Klebsiella. In this method, at least the upstream regulatory region of the bud operon, a DNA region which is located 5' of the structural gene and which possesses a regulatory function with respect to the expression of the structural gene, is isolated from such an organism in a manner known per se. Where appropriate, the parts which are isolated concomitantly, and which do not possess any regulatory function, are removed using known methods (See Example 14).

Preferably, a DNA fragment containing the promoter is isolated from a gene library of a bacterium of the genus Enterobacter or Klebsiella, particularly preferably from a gene library of *Klebsiella terrigena* (DSM2687).

The invention also relates to an expression cassette wherein a promoter which is suitable for the expression system is linked functionally to the structural gene of a recombinant protein which is to be expressed.

In a preferred embodiment of the expression cassette, a transcribed, but untranslated, region which contains a ribosome binding site is located between the promoter region and the structural gene which is to be expressed.

An expression cassette according to the invention can be prepared, for example, by the promoter being cloned, in a manner which is known to a person skilled in the art, upstream of the 5' end of a structural gene which is to be expressed.

The invention furthermore relates to microorganisms which contain an expression cassette according to the invention.

While the expression cassette can, in this context, be integrated into the genome of the microorganism, it can also be present episomally on at least one vector. Preferably, the expression cassette is present episomally on at least one vector.

In the first-mentioned embodiment, the novel expression cassette is integrated into the genome of the host organism using known methods.

In the preferred embodiment, which was mentioned as the second embodiment, the expression cassette is present episomally in the host organism on a vector, the so-called expression vector. The novel expression cassette is integrated into a vector using the customary methods which are known to a person skilled in the art. Suitable vector molecules are known to the person skilled in the art. An example of such a vector is the vector pJF118, which is known to the person skilled in the art (Fürste et al. (1986), *Gene* Vol. 48, pp. 119–131), and derivatives thereof.

The invention furthermore relates to a process for preparing an expression system according to the invention, wherein, where appropriate, at least one gene for a regulator protein according to the invention and/or, where appropriate, at least one expression cassette according to the invention are introduced into any desired microorganism so that at least one gene for a regulator protein according to the invention and an expression cassette according to the invention are subsequently present in the relevant microorganism.

The invention also relates, therefore, to microorganisms which contain an expression system according to the invention.

The novel expression system can be prepared, for example, by introducing an expression cassette according to the invention into any desired microorganism which contains at least one gene for a regulator protein according to the invention.

Preferably, in this process for preparing the novel expression system, those microorganisms are used which naturally contain a gene for a regulator protein according to the invention.

Particular preference is given, in this process, to microorganisms of the genera Enterobacter or Klebsiella which contain a gene for a regulator protein according to the invention.

*Klebsiella terrigena* (DSM2687) is particularly preferably used in this process.

Furthermore, those microorganisms are particularly preferably used in this process as host strains for an expression cassette according to the invention which have been supplied with a gene for a regulator protein according to the invention in a manner which is known to a person skilled in the art. In this context, the gene which has been supplied, and which encodes the regulator protein, can be present episomally or be integrated into the host chromosome.

If the supplied gene, which encodes the regulator protein, is present episomally, it will preferably be located on the same vector molecule which also carries the expression cassette. In addition, however, an arrangement is also preferred in which the supplied gene for a regulator protein according to the invention and the novel expression cassette are present, simultaneously in a cell of the host organism, on two different, but complementary, vector molecules, as is known to a person skilled in the art.

In a general embodiment, gram-positive or gram-negative bacteria are used as host strains for the construction of expression systems in which the host strain has additionally been supplied with a gene which encodes the regulator protein.

Bacteria of the family Enterobacteriaceae, particularly preferably those of the genera Escherichia and Salmonella, are preferably used as host strains for such an expression system. Particular preference is given to the use of *Escherichia coli* as the host strain for such an expression system.

The present invention furthermore relates to the use of Fnr-negative microorganisms as the host strain for an expression system according to the invention. Microorganisms which are naturally Fnr-negative are preferably used. Particular preference is given to the use of those microorganisms as host strains for an expression system according to the invention in which the fnr gene has been inactivated using methods which a re known to the person skilled in the art. An example of such a particularly preferred microorganism is *E. coli* RM101 (Sawers and Suppmann, (1992), *J. Bacteriol.* Vol. 174, pp. 3474–3478) and all the derivatives derived therefrom.

The invention also relates to fermentation processes for producing proteins using microorganisms, wherein microorganisms are used which contain the novel expression system.

If a maximal induction effect to be achieved in a fermentation according to the invention, a microorganism which contains an expression system according to the invention is cultured at pH values>pH 7.0 under aerobic conditions and without external addition of acetate. It is then possible, at arbitrary time points, to induce the expression of a gene for a recombinant protein which is part of the novel expression cassette maximally by limiting the oxygen partial pressure, $pO_2$, to values of 0 to 5%, regulating the pH of the medium to pH 6.0 to 6.5, and adding acetate to a final concentration of 40 mM to 60 mM.

Over and above this, it is possible, in a simple manner, by suitably combining different set values for these three stimuli, to induce the expression of the gene fusion in intermediate steps which can be graded from being very shallow to being very steep. As a rule, the option of achieving a precisely graded induction is very desirable since it is thereby possible, for example, to adjust the expression level such that just that quantity of target protein is formed at which the protein still does not precipitate out as so-called inclusion bodies.

An example of an induction condition which leads to a very weak induction is the combination pH>pH 6.5, external addition of acetate (to 40 mM) and the presence of oxygen having a partial pressure, $pO_2$, of greater than 10%.

An advantage of the novel expression system is that it also enables expression of appropriate gene fusions to be strongly induced in the presence of oxygen (pO$_2$>5%) by means of reducing the pH of the culture medium to pH 6.0 and adding acetate (40 to 60 mM).

BRIEF DESCRIPTION OF THE DRAWINGS

Other objects and features of the present invention will become apparent from the following detailed description considered in connection with the accompanying drawings which discloses several embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
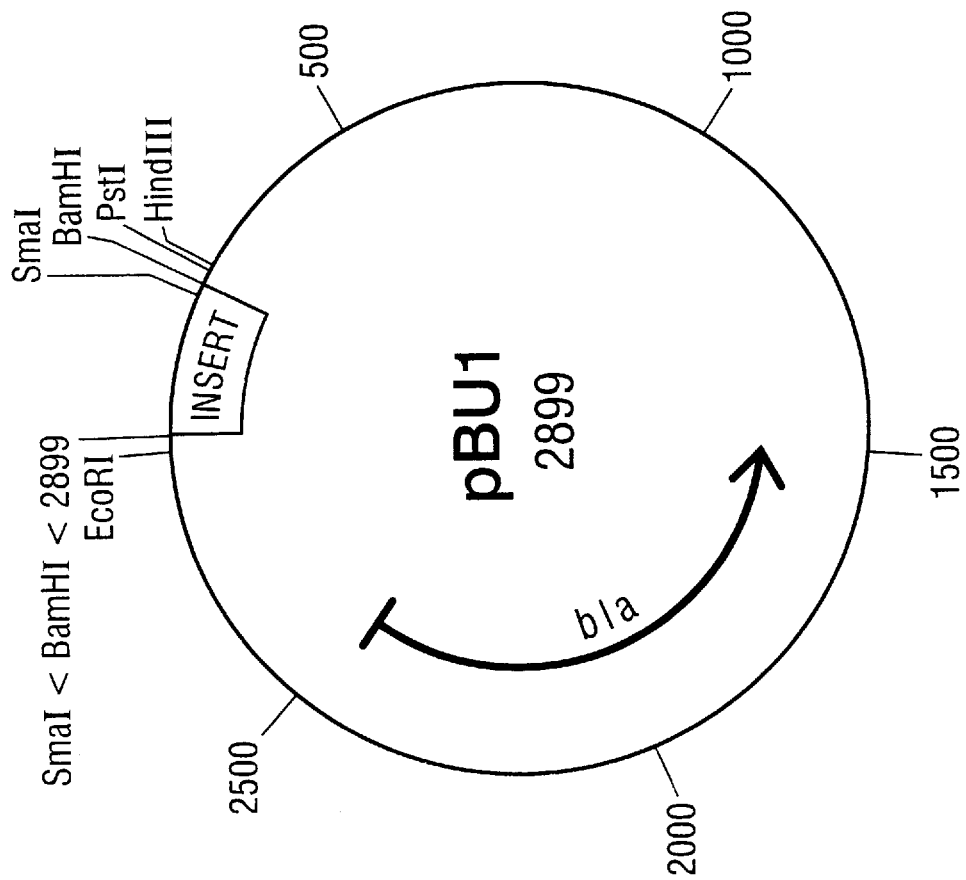
FIG. 1 shows the plasmid map of pBU1.

General remarks on the construction of the plasmids used in the examples and the expression studies.

1. All anaerobic cultivations were carried out in serum bottles in accordance with Balch and Wolfe (1976), *Appl. Environ. Microbiol.* Vol. 32, pp. 781–791. Aerobic cultures took place in Erlenmeyer flasks which were shaken vigorously (at most ¹⁄₁₀ of the given volume was added to the flasks). The cultures were incubated at 37° C.

2. Medium for aerobic cultures: TGYEP (1% tryptone, 0.5% yeast extract, 0.4% glucose, 100 mM K phosphate, pH values adjusted to 6.0 to 8.0 using 0.1 M potassium phosphate buffer); medium for aerobic cultures: TGYEP (pH adjusted as described above); addition of the inducer Na acetate to 40 mM from a 1 M stock solution.

The media described by Kleckner et al. ((1978), *Genetics* Vol. 90, pp. 427–450) were employed for the work with phage.

3. Antibiotics were added in the following concentrations: ampicillin, 100 μg/ml; chloramphenicol, 30 μg/ml; kanamycin, 50 μg/ml; tetracycline, 20 μg/ml or 15 μg/ml for chromosomally encoded resistances:

4. Chromosomal DNA was prepared by the method of Ausubel et al. ((1987), *Current Protocols in Molecular Biology*, Vol. 1, Greene Publishing Associates and Wiley-Interscience, N.Y.), Plasmid DNA was prepared by the method of Holmes and Quigley ((1981), *Anal. Biochem* Vol. 114, pp. 193–197).

5. Unless otherwise indicated, the strains which were used were transformed with plasmid DNA in accordance with standard procedures (Maniatis et al. (1982) *Molecular Cloning, A Laboratory Manual*, Cold Spring Harbor Laboratory, Cold Spring Harbor, N.Y., pp. 249–255).

6. The β-galactosidase activity was determined in accordance with Miller (1972) *Experiments in Molecular Genetics*, Cold Spring Harbor Laboratory, Cold Spring Harbor, N.Y. pp. 352–355. The enzyme activities are given in Miller units.

7. A lac mutant of *Klebsiella terrigena* DSM2687 was produced by random UV mutagenesis in accordance with Miller (1972) *Experiments in Molecular Genetics*, Cold Spring Harbor Laboratory, Cold Spring Harbor, N.Y., pp. 121–124. Irradiation took place for 80 seconds at an intensity of 318 μW/cm$_2$. The stability of the mutation was tested for reversions by incubating with nitrosoguanidine (Miller (1972) *Experiments in Molecular Genetics*, Cold Spring Harbor Laboratory, Cold Spring Harbor, N.Y., pp. 125–129). After having checked the metabolic reactions which are typical for Klebsiella, the strain KT14 was chosen for the subsequent investigations.

8. The budA–lacZ fusions were integrated into the *E. coli* chromosome using the method of Simons et al. (1987), *Gene* Vol. 53, pp. 85–96. Starting with the strain *E. coli* MC4100 (F-, araD139, D(argF-lac)U169, ptsF25, deoC1, re1A1, flbB5301, rpsL150, λ-) (Casadaban and Cohen (1979), *Proc. Nat. Acad. Sci. USA*, Vol. 76, pp. 4530–4533), the following transductants were obtained: BL142 and BL2. The strain BL12 was obtained by transduction from the strain *E. coli* RM101 (fnr-) (Sawers and Suppmann (1992) *J. of Bacteriology* 174, 11 pp. 3474–3478).

9. Unless otherwise indicated, in-vitro enzymic reactions on DNA were carried out in accordance with Maniatis et al. (1982), *Molecular cloning, A Laboratory Manuary*, Cold-Spring Harbor Laboratory, Cold Spring Harbor, N.Y., pp. 98–148.

Starting vectors:

1. pUC19 (Yanisch-Perron et al. (1985), *Gene* Vol. 33, pp. 103–119);

2. pBR322 (Bolivar et al. (1977), *Gene* Vol. 2, pp. 95–113);

3. pRS552 (Simons et al. (1987), *Gene* Vol. 53, pp. 85–96);

4. pJF118HE (Fürste et al. (1986), *Gene* Vol. 48, pp. 119–131);

5. pCM100 (Binder et al. (1986), *Gene* Vol. 47, pp. 269–277);

Phage:

λRS45 (Simons et al. (1987), *Gene Vol.* 53, pp. 85–96)

10. Synthetic oligonucleotides were obtained from Toplab (Martinsried, Germany). The nucleotide sequences of the oligonucleotides used in the examples are presented together in Table 1:

TABLE 1

Nucleotide sequences of the oligonucleotides employed

| SEQ ID NO: | Designation |
|---|---|
| 7 | Oligo1 |
| 8 | Oligo2 |
| 9 | Oligo3 |
| 10 | Oligo4 |
| 11 | Oligo5 |
| 12 | Oligo6 |
| 13 | Oligo7 |
| 14 | Oligo8 |
| 15 | Oligo9 |

11. Enzymes for restricting, modifying and analyzing the sequence of DNA were obtained from Boehringer Mannheim GmbH (Mannheim), Pharmacia (Freiburg), New England Biolabs (Schwalbach) and Perker Elmer Cetus (Langen).

Radioactive substances came from Amersham Buchler (Braunschweig) or NEN Du Pont (Dreieich).

Fine chemicals were obtained from Merck (Darmstadt), Sigma (Munich), Serva (Heidelberg), Fluka (Neu-Ulm) and Biomol (Munich).

Other objects and features of the present invention will become apparent from the following Examples, which disclose the embodiments of the present invention. It should be understood, however, that the Examples are designed for the purpose of illustration only and not as a definition of the limits of the invention.

EXAMPLE 1

Translational coupling of the budA promoter fragment to the lacZ gene

Using the oligonucleotides Oligo1 and Oligo2 (Table 1), whose nucleotide sequence was derived from the sequence of the *Klebsiella terrigena* bud operon published by Blomqvist et al. (*J. Bact.* (1993) Vol. 175(5), pp. 1392–1404), a 223 bp-sized fragment from *Klebsiella terrigena* (DSM2687) chromosomal DNA was amplified by symmetrical PCR (annealing: 30 s at 58° C.; chain elongation: 60 s at 72° C.; strand separation: 30 s at 94° C.; 25 cycles). The resulting fragment extends over positions 247 to 456 of the nucleotide sequence SEQ ID NO:2 and contains the sequence information for the 10 N-terminal amino acid residues of BudA (See FIG. 7A), and also 178 nucleotides which are located upstream of the budA start codon and which contain the functionally active promoter of the bud operon.

Following cleavage of the PCR with BamHI, using the BamHI restriction recognition sites which were introduced by the PCR starting nucleotides oligo1 and Oligo2, a 219 bp-sized DNA fragment was isolated and cloned into vector pUC19 which had been cut with BamHI. The correctness of the nucleotide sequence, and also the orientation of the insert, were checked by double-stranded sequence analysis (Sanger et al. (1977) *Proc. Natl. Acad. Sci.* USA 74(12), pp. 5463–5467). The resulting construct was termed pBU1 (FIG. 1).

Figure 2:
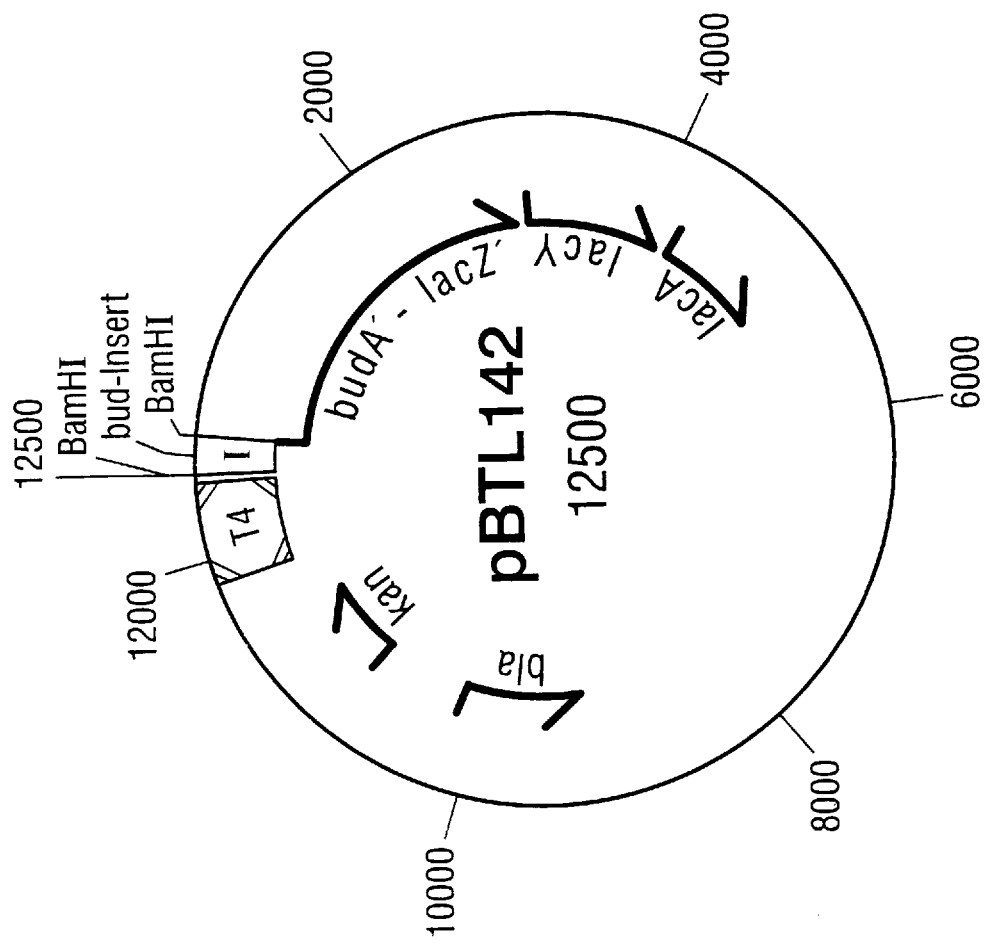
FIG. 2 shows the plasmid map of pBTL142.

In order to combine the bud promoter on pBU1 with the lacZ gene as reporter gene for promoter activity, the BamHI fragment from pBU1 was subcloned into the BamHI cleavage site of the promoter test vector pRS552. The resulting construct, plasmid pBTL142 (FIG. 2), encodes a fusion protein similarly which consists of the 10 N-terminal amino acid residues of BudA and, connected to them by way of a linker consisting of 2 amino acid residues, LacZ from the 9th amino acid residue (FIG. 3, SEQ ID NO:3 and SEQ ID NO:4), whose transcription can only be regulated by the regulatory elements which are contained in the 178 bp upstream of budA.

EXAMPLE 2

Expression of β-galactosidase protein by the bud promoter fragment of pBTL142 in Klebsiella terrigena KT14

In order to carry out a functional investigation of the bud promoter on pBTL142 in *Klebsiella terrigena* (homologous system), *Klebsiella terrigena* KT14 (lacZ-) was transformed with pBTL142 by means of electroporation (Fiedler and Wirth (1988) Analytical Biochemistry 170, pp. 38–44). A transformant (*Klebsiella terrigena* KT14/pBTL142) which was obtained in this way was cultured for expression studies under the conditions given in Table 2. The β-galactosidase activities which were generated under these circumstances (Table 2), and which were determined in cell lysates in accordance with Miller, are a direct measure of the activity of the bud promoter under the respective conditions.

TABLE 2

Expression of budA'-lacZ' in *Klebsiella terrigena* KT14/pBTL142

| pH | $+O_2$ | $+O_2$ + acetate | $-O_2$ | $-O_2$ + acetate |
|---|---|---|---|---|
| 6.0 | 668 | 5688 | 2300 | 11515 |
| 6.5 | 800 | 2272 | 1057 | 4326 |
| 7.0 | 833 | 1280 | 760 | 1533 |
| 7.5 | 884 | 1123 | 784 | 754 |
| 8.0 | 875 | 1003 | 741 | 743 |

EXAMPLE 3

Expression of β-galactosidase protein in *Klebsiella terrigena* KT14/pBTL142 while fermenting under inducing and non-inducing conditions Fermenter type: Biostat ED (B.Braun Biotech, Melsungen, Germany).

Charging volume: 7 l.

Medium: $KH_2PO_4$: 1.5 g/l; $(NH_4)_2SO_4$: 5.0 g/l; NaCl: 0.5 g/l; $FeSO_4 \times 2H_2O$: 0.075 g/l; $Na_3$ citrate$\times 2H_2O$: 1.0 g/l; Tryptone (Oxoid): 5 g/l; yeast extract (Oxoid): 2.5 g/l; glucose: 12 g/l; kanamycin: 50 mg/l pH of the medium: constantly 6.0 (corrected with 6N $NH_4OH$, or 4N $H_3PO_4$)

Temperature: 30° C.

Aeration: the cultures were aerated in a constant manner, over the whole of the course of the fermentation, with 4 l of air per minute. Until an optical density of $OD_{600}=20$ had been reached, a constant oxygen partial pressure of $pO_2=40\%$ was maintained by stirring at speeds of between 450 and 900 rpm. Once $OD_{600}=20$ had been reached, the $pO_2$ was adjusted to $pO_2=0\%$ within the time span of one hour by means of reducing the speed of stirring, and kept at this value for 48 h.

Induction: once $pO_2=0\%$ had been reached, acetate was added to the fermenters which were to be induced to give a final concentration of 40 mM.

The β-galactosidase activities were determined at 24 h and 48 h after induction.

TABLE 3

Expression of budA'-lacZ' in *Klebsiella terrigena* KT14/pBTL142
β-Galactosidase activity (Miller units)

|  | 24 h | 48 h |
|---|---|---|
| Without induction | 460 | 700 |
| With induction | 10820 | 15325 |

EXAMPLE 4

Expression of β-galactosidase protein in *E. coli* FM420 by the budA promoter fragment on pBTL142

The values given in Table 4 were determined in subsequent expression studies after having transformed *E. coli* FM420 with pBTL142.

TABLE 4

Expression of budA'-lacZ' in *E. coli* FM420/pBTL142

| pH | +O$_2$ | -O$_2$ | -O$_2$ + acetate |
|---|---|---|---|
| 6.0 | 424 | 408 | 737 |
| 7.0 | 613 | 466 | 722 |
| 8.0 | 655 | 607 | 794 |

No significant induction of the bud promoter can be detected in the heterologous system. *E. coli* does not possess the transcription factors which are required for full expression and regulation, i.e. the cis-acting factors which are present on pBTL142 are not, by themselves, sufficient to produce in *E. coli* the expression behavior which is observed in *Klebsiella terrigena* (EXAMPLE 2).

EXAMPLE 5

Integration of the budA'-lacZ' translation fusion on plasmid pBTL142 into the genome of *E. coil* MC4100

The budA'-lacZ' fusion was integrated into the chromosome using the method of Simons et al. ((1987), *Gene* Vol. 53, pp. 85–96). The translation fusion was integrated into the *E. coil* MC4100 chromosome by means of transforming pBTL142 into *E. coli* MC4100 and then infecting with λRS45. Successful integration was tested for on the basis of the kanamycin resistance which had been transduced. Lysates of λBTL142 which were obtained following UV irradiation (purified phage line) were used to transduce *E. coli* MC4100 once again and the strain which was constructed in this manner was designated *E. coli* BL142.

EXAMPLE 6

Expression of budA'–lacZ' in *E. coli* BL142 by the chromosomally integrated gene All cultivations were carried out at pH 6.5.

TABLE 5

Expression of budA'-lacZ' in *E. coli* BL142

| Growth conditions | β-Galactosidase activity |
|---|---|
| +O$_2$ | 35 |
| -O$_2$ | 40 |
| -O$_2$ + acetate | 70 |

While a slight basal expression can be detected under the given growth conditions, it is not possible to detect any significant induction by anaerobiosis and the addition of acetate.

EXAMPLE 7

Cloning a gene from *Klebsiella terrigena* which encodes a protein which activates the budA promoter in *E. coli*

Chromosomal DNA was isolated from *Klebsiella terrigena* DSM 2687 and subjected to partial digestion with Sau3A (0.02 units/µg of DNA, 20 min at 37° C.). Fragments of between 3 and 10 kb were isolated following electrophoretic fractionation and ligated into the BamHI-linearized vector pBR322. The plasmid pool which was obtained following transformation of *E. coli* JM109 and subsequent preparation was used as a *Klebsiella terrigena* gene library.

Figure 4:
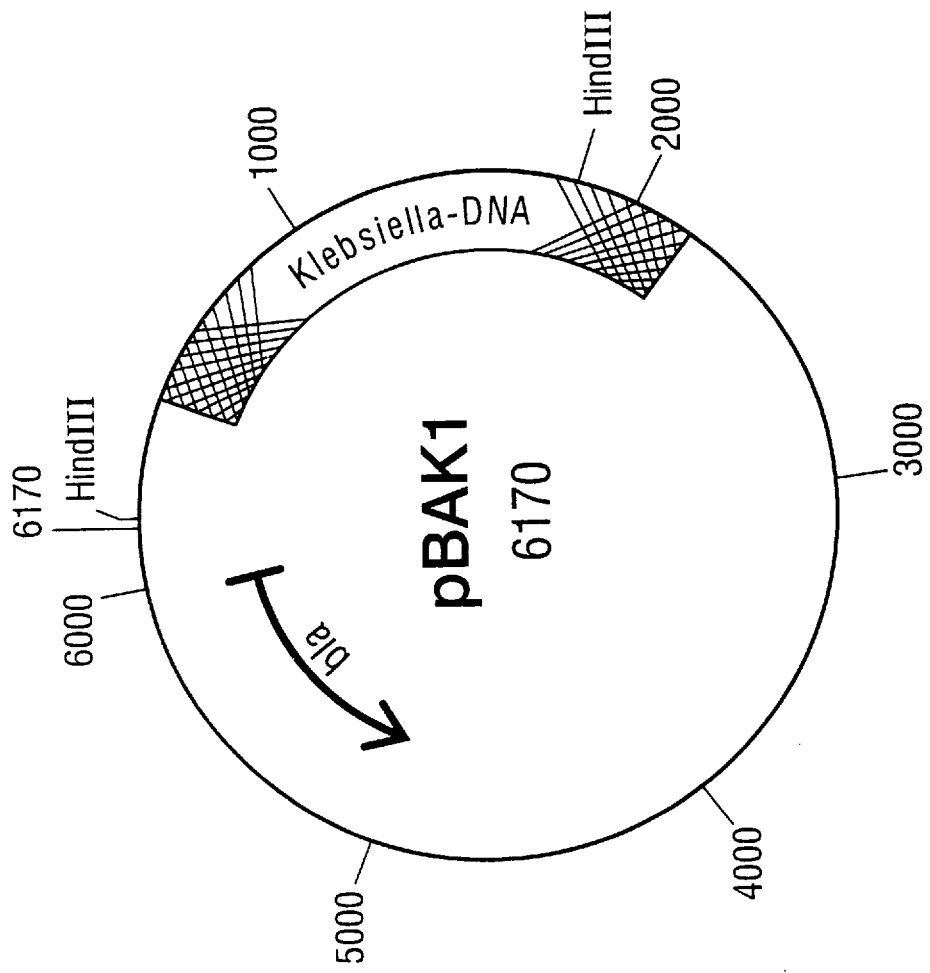
FIG. 4 shows the plasmid map of pBAK1.
Figure 5:
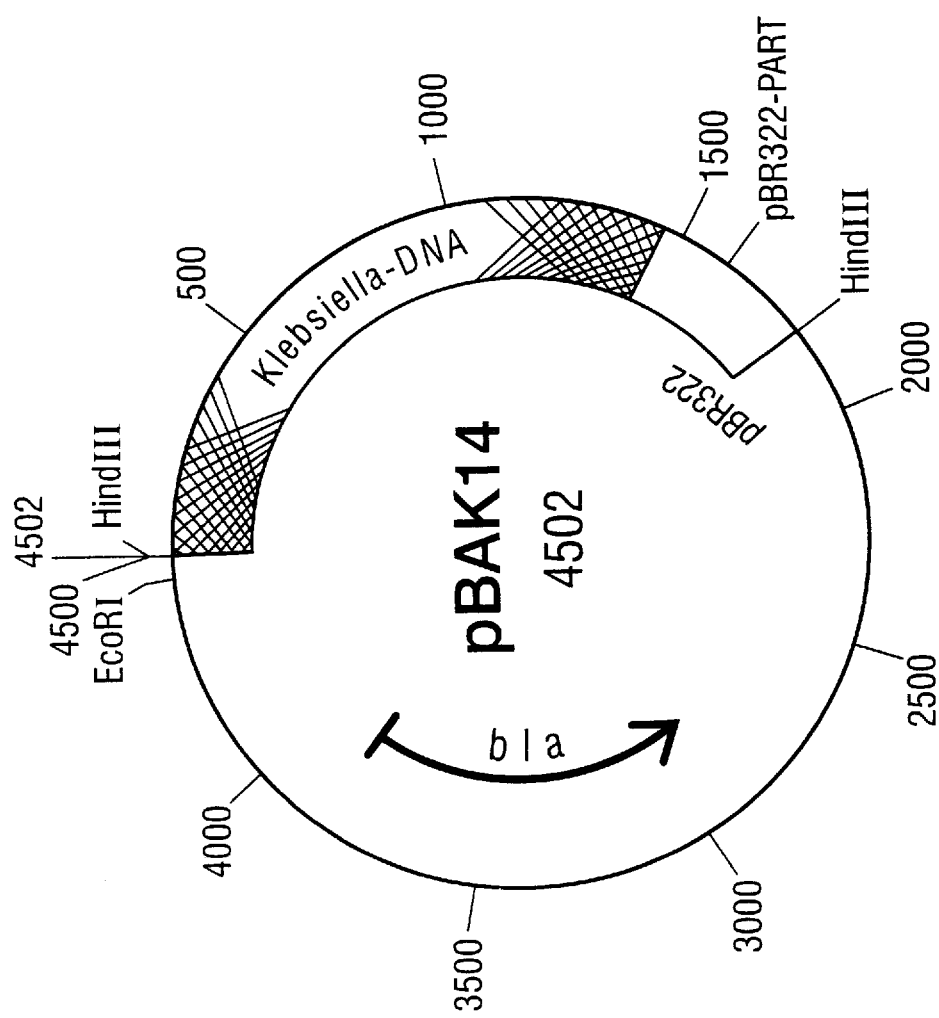
FIG. 5 shows the plasmid map of pBAK14.
Figure 6:
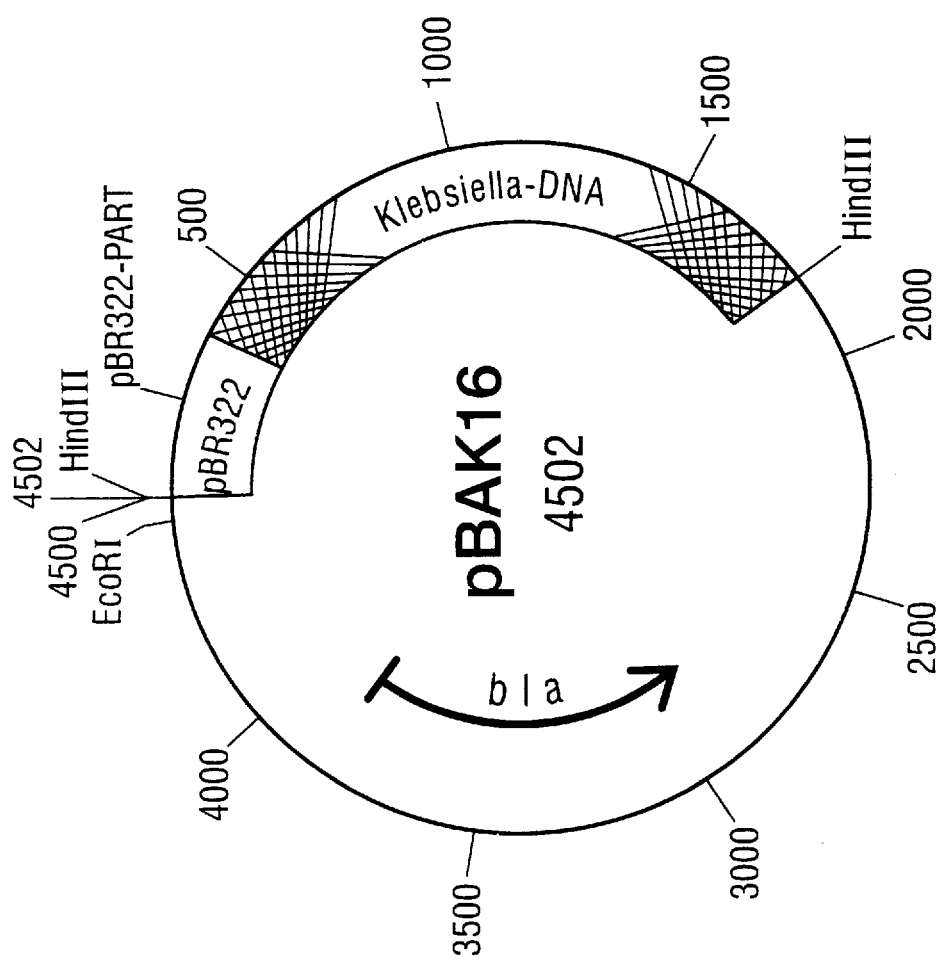
FIG. 6 shows the plasmid map of pBAK16.

In order to identify plasmids encoding a transacting factor which activates the bud promoter in the presence of acetate, *E. coli* BL142 was transformed with the *Klebsiella terrigena* gene library by means of electroporation (Fiedler and Wirth (1988) Analytical Biochemistry 170, pp. 38–44). The transformation mixtures were spread on so-called indicator plates (potassium phosphate-buffered TGYEP agar (pH 6.5) containing 0.4% glucose, 40 mM acetate, 1 mM X-Gal and ampicillin (100 µg/ml)) and were incubated at 37° C. Due to its very weak β-galactosidase activity (Table 5), *E. coli* BL142 forms pale-blue colonies on these indicator plates. By contrast, after transformation, one clone formed a deep dark blue colony. It contained the plasmid pBAK1 (FIG. 4), which carries an approximately 1.8 kb-sized Sau3A fragment from *Klebsiella terrigena*. For the subsequent analyses, a 1.8 kb-sized HindIII fragment, which contains a 350 bp-sized fragment of vector pBR322 and a 1.45 kb-sized fragment from *Klebsiella terrigena*, was isolated from pBAK1 (See FIG. 4); the protruding ends of the fragment were filled in with Klenow polymerase. The fragment was then ligated, in both orientations, into plasmid pUC19 which had been linearized with SmaI. The resulting plasmids, which also impart a blue coloration to *E. coli* BL142 colonies on indicator plates, were designated pBAK14 and pBAK16 (FIGS. 5 and 6).

EXAMPLE 8

Analysis of the sequence of the gene for the budA promoter-activating regulator protein on pBAK14 and pBAK16

In order to analyze the sequence of the insert on pBAK14 and pBAK16 using the method of Sanger et al. ((1977),

*Proc. Natl. Acad. Sci. USA* Vol. 74, pp. 5463–5467), the inserts were in each case truncated using exonuclease III. Restriction with SacI was used to protect the vector, and exonuclease attack took place at an Asp718 cleavage site of the multiple cloning site in pUC19 (Henikoff (1984), *Gene* Vol. 28, pp. 351–359). The sequencing reactions using T7 DNA polymerase (Pharmacia, Freiburg) were carried out in parallel using dGTP and dITP in order to avoid strong compression. A commercially available universal sequencing starting oligonucleotide was used which was specific for pUC vectors. Then the nucleotide sequence (SEQ ID NO:2) was determined for the *Klebsiella terrigena* DNA insert on pBAK14 and pBAK16.

From the nucleotide sequence which was determined (SEQ ID NO:2), it was possible to deduce an open reading frame (nucleotides 385 to 1254) which encodes a protein (SEQ ID NO:1) consisting of 290 amino acids. The amino acid sequence which was deduced from this open reading frame was SEQ ID NO:1.

Figure 7:
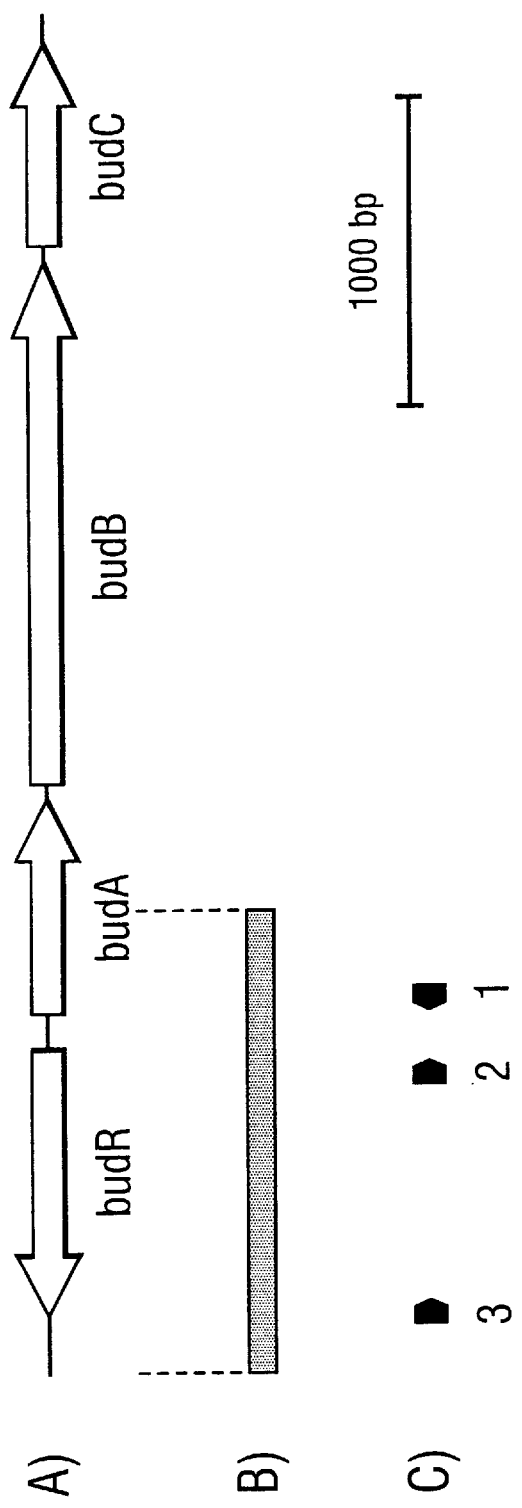
FIG. 7A shows the size and relative orientation of the genes of the bud regulon in the genome of Klebsiella terrigena (DSM2687)
FIG. 7B shows the DNA fragment contained on pBAK14 and pBAK16.
FIG. 7C shows the position of the oligonucleotides used for the PCR amplification of Klebsiella DNA (See Examples 1 and 10)

Because of its activity in regulating the activity of the bud promoter, this protein was designated BudR (bud regulator). While the direction in which budR is transcribed is opposite to that for transcribing the bud operon, there is, nevertheless, only an intergenic region of a mere 106 bp (nucleotides 279 to 384 in SEQ ID NO:2) between bud operon and budR. Consequently, bud operon and budR form a divergently oriented regulon for synthesizing the enzymes which are involved in the formation of 2,3-butanediol (FIG. 7).

EXAMPLE 9

Expression of β-galactosidase protein by the chromosomally located budA'–'lacZ translation fusion in *E. coli* BL142/pBAK1

The ability of the chromosomally encoded budA'–'lacZ fusion to be induced by plasmids from the gene bank, which elicit a lac+ phenotype (blue coloration), will be demonstrated using the following example. All the cultures took place at pH 6.5.

TABLE 6

Expression of budA'-lacZ' in *E. coli* BL142/pBAK1

| Growth conditions | β-Galactosidase activity |
|---|---|
| $+O_2$ | 1832 |
| $-O_2$ | 1147 |
| $-O_2$ + acetate | 5802 |

EXAMPLE 10

Figure 8:
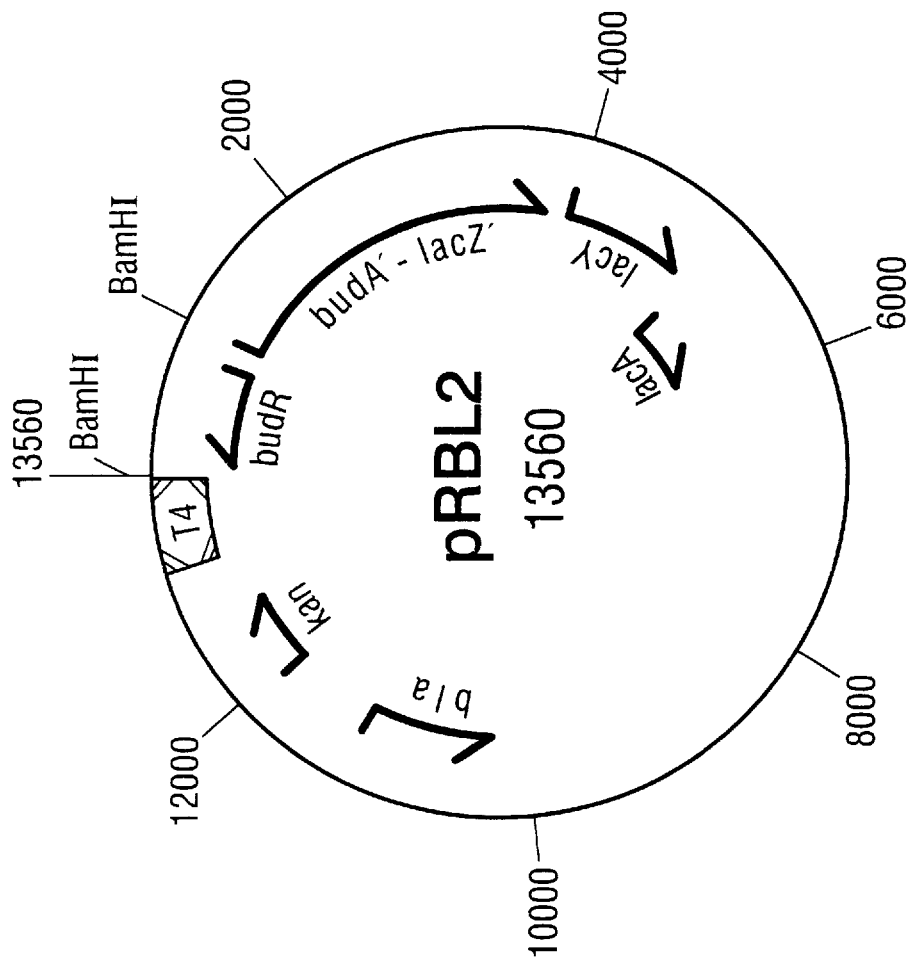
FIG. 8 shows the plasmid map of pRBL2.

Construction of the budA'–lacZ' fusion together with the complete sequence of budR and the intergenic region between the budR and budA Using the oligonucleotides Oligo1 and Oligo3 (Table 1), a 1027 bp-sized fragment was amplified from pBAK16 (pUC19 derivative) by means of symmetrical PCR (FIG. 7). Following cleavage of the PCR product with BamHI, using the BamHI restriction recognition sites which were introduced by the PCR starting nucleotides Oligo1 and Oligo3, a 1023 bp-sized DNA fragment was isolated and cloned into vector pRS552, which had been cut with BamHI. The correctness of the orientation of the insert was tested for by sequence analysis in accordance with Sanger et al. ((1977), *Proc. Natl. Acad. Sci, USA* Vol. 74, pp. 5463–5467). The resulting construct was termed pRBL2 (FIG. 8).

Figure 3:
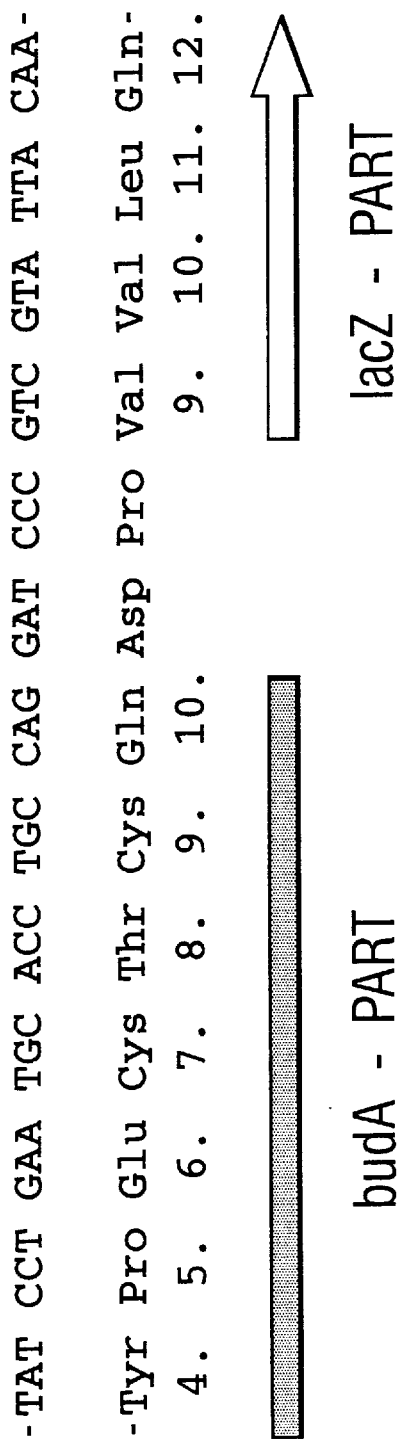
FIG. 3 shows the nucleotide sequence (SEQ ID NO:3); and the amino acid sequence (SEQ ID NO:4) of the budA'–lacZ' junction on pBTL142 and pRBL2.

Plasmid pRBL2 contains the complete gene for BudR, the complete intergenic region between budR and budA, and the gene which encodes a fusion protein and which consists of the 10 N-terminal AA residues of BudA and, connected thereto by way of a linker consisting of 2 amino acid residues, LacZ from the 9th amino acid residue, which gene is also contained on pBTL142 (FIG. 3).

EXAMPLE 11

Integration of budR into the genome of *E. coli* MC4100

The budA'–lacZ' fusion possessing the additional sequence of budR, on plasmid pRBL2, was integrated into the *E. coli* MC4100 chromosome using the method of Simons et al. (1987), *Gene* Vol. 53, pp. 85–96. The fusion was integrated into the *E. coil* MC4100 chromosome by transforming pRBL2 into *E. coli* MC4100 and then infecting *E. coli* MC4100/pRBL2 with λRS45. Successful integration was tested for on the basis of transduced kanamycin resistance. The lysates of RBL2 which were obtained following UV irradiation (purified phage lines) were used to transduce *E. coli* MC4100 once again, and the strain which was constructed in this way was termed *E. coli* BL2.

EXAMPLE 12

Expression of β-galactosidase protein by the chromosomally located budA'–lacZ' fusion in *E. coli* BL2

The regulation of the expression of the budA' lacZ' gene fusion in the *E. coli* chromosome which was achieved by means of the single copy of budR is shown in Table 7. All the cultures took place in TGYEP medium at pH 6.5.

TABLE 7

Expression of budA'-lacZ' in *E. coli* BL2

| Growth conditions | β-Galactosidase activity |
|---|---|
| $-O_2$ | 99 |
| $-O_2$ + acetate | 1130 |

EXAMPLE 13

Expression of β-galactosidase protein in *E. coli* BL2/pBTL142

Induction of the plasmid-encoded budA'–lacZ' gene fusion by the chromosomally encoded BudR is shown in Table 8.

TABLE 8

Expression of budA'-lacZ' in *E. coli* BL2/pBTL142

| pH | $+O_2$ | $+O_2$ + acetate | $-O_2$ | $-O_2$ + acetate |
|---|---|---|---|---|
| 6.0 | 1435 | 10114 | 1520 | 14413 |
| 6.5 | 1410 | 6907 | 928 | 5381 |
| 7.0 | 1403 | 2257 | 980 | 1968 |
| 7.5 | 1281 | 1440 | 960 | 1339 |
| 8.0 | 1265 | 1665 | 1135 | 1243 |

EXAMPLE 14

Step-wise deletion of the 5' region of the budA promoter region on plasmid pBTL142

In order to determine the minimum nucleotide region of the bud promoter which still possesses a promoter activity which can be activated by BudR, the promoter present on plasmid pBTL142 was truncated step-wise starting from its 5' end. To do this, pBU1 was linearized at the 5' end of the insert by restricting with EcoRI and was incubated at 30° C. with Bal131 exonuclease (Boehringer Mannheim) (0.3 units/μg of DNA) (Schaffner et al., 1976). The 5'-protruding DNA ends were filled in with the Klenow fragment of DNA polymerase I and provided with EcoRI linkers (Oligo4 (Table 1)). Following restriction with EcoRI and BamHI, the fragments were fractionated by electrophoresis and fragments of the appropriate length were eluted and inserted into vector pRS552, which had been treated beforehand with EcoRI and BamHI. The 5' ends of the inserts in the deletion constructs were determined by sequence analysis. Selected clones (pBTL6 to pBTL124) are listed in Table 9.

TABLE 9

Sizes of the bud promoter moieties on plasmids pBTL6 to pBTL142

| Plasmid | Size of the promoter moiety (bp) | (bp) from position 315 to position xxx in SEQ ID NO: 10 |
|---|---|---|
| pBTL6 | 6 | 320 |
| pBTL22 | 22 | 336 |
| pBTL34 | 34 | 348 |
| pBTL51 | 51 | 365 |
| pBTL64 | 64 | 378 |
| pBTL83 | 83 | 397 |
| pBTL103 | 103 | 407 |
| pBTL124 | 124 | 438 |
| pBTL142 | 142 | 456 |

EXAMPLE 15

Expression of β-galactosidase protein by the truncated budA promoter fragments on plasmids PBTL 6 to pBTL142

Expression studies using the truncation clones were carried out in *Klebsiella terrigena* KT14 as the host strain. All the cultures took place at pH 6.5.

TABLE 10

Expression of budA'-lacZ' in *Klebsiella terrigena* KT14/pBTL6–pBTL142

| Plasmid | $+O_2$ | $+O_2$ + acetate | $-O_2$ | $-O_2$ + acetate |
|---|---|---|---|---|
| pBTL6 | 30 | 49 | 18 | 30 |
| pBTL22 | 52 | 136 | 41 | 120 |
| pBTL34 | 34 | 70 | 24 | 84 |
| pBTL51 | 264 | 645 | 205 | 523 |
| pBTL64 | 252 | 677 | 214 | 624 |
| pBTL83 | 398 | 2575 | 967 | 5563 |
| pBTL103 | 211 | 1675 | 752 | 4703 |
| pBTL124 | 238 | 1849 | 828 | 4444 |
| pBTL142 | 449 | 2040 | 767 | 3145 |

EXAMPLE 16

Expression of β-galactosidase protein in *E. coli* BL12 and *E. coli* BL12/pUFR1

In order to investigate the influence of the *E. coli*-specific inducer of anaerobic metabolism, Fnr, on the BudR-dependent activation of the bud promoter, budR and the budA'-lacZ' translation fusion on plasmid pRBL2 (FIG. 8) wereintegrated into the chromosome of the fnr-negative *E. coli* RM101 by means of transducing the μRS45 in analogy with the procedure described in EXAMPLE 11. The resulting strain was designated *E. coli* BL12. In order to investigate possible Fnr effects, *E. coli* BL12 was additionally transformed with the plasmid pUFR1, which carries a functional fnr gene (Sawers and Suppmann (1992) *J. of Bacteriology* 174, 11 pp. 3474–3478).

TABLE 11

Expression of budA'-lacZ' in *E. coli* BL12 and BL12/pUFR1

| Strain/plasmid | Growth conditions | β-galactosidase activity |
|---|---|---|
| BL12 | $-O_2$ | 371 |
| BL12 | $-O_2$ + acetate | 3700 |
| BL12/pUFR1 | $-O_2$ | 115 |
| BL12/pUFR1 | $-O_2$ + acetate | 509 |

EXAMPLE 17

Functional coupling of the bud regulatory system to the alpha-CTGase structural gene The oligonucleotides Oligo5 to Oligo9, which are given in Table 1, were used to construct the CGTase expression plasmid pBUD200.

A) Construction of pBUD100

With the aid of oligonucleotides Oligo5 and Oligo6 (Table 1), and using plasmid pBAK16 as the template DNA, a DNA fragment containing the complete budR gene and the budA promoter (nucleotides 281 to 1300 in SEQ ID NO:2) was amplified by means of PCR and cleaved with the restriction endonucleases NruI and NcoI.

Oligonucleotides Oligo7 and Oligo8 (Table 1) were used as the starting oligonucleotides, and plasmid pCM100 (Binder et al. (1986), Gene Vol. 47, pp. 269–277) was used as the template DNA, in order to amplify the structural gene for Klebsiella Oxytoca M5a1 alpha-CTGase. The amplified DNA fragment was cleaved with the restriction endonucleases NcoI and EcoRI.

Figure 9:
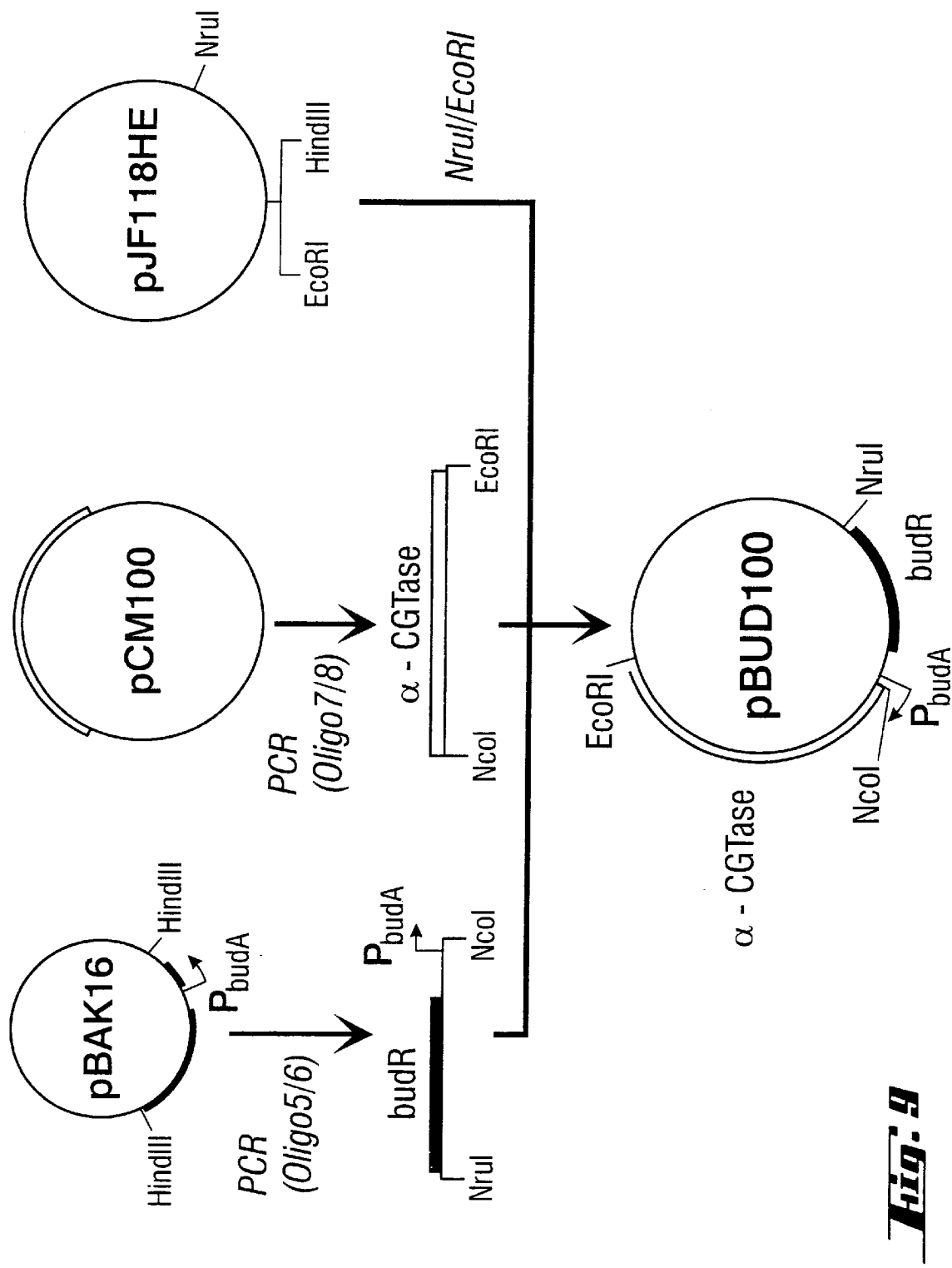
FIG. 9 shows the construction of pBUD100 (See Example 17)

The two PCR fragments were together ligated and the vector pJF118HE, which had been cleaved with NruI and EcoRI (FIG. 9). The resulting plasmid is designated pBUD100.

B) Construction of pBUD200 by means of site-directed mutagenesis

Figure 10:
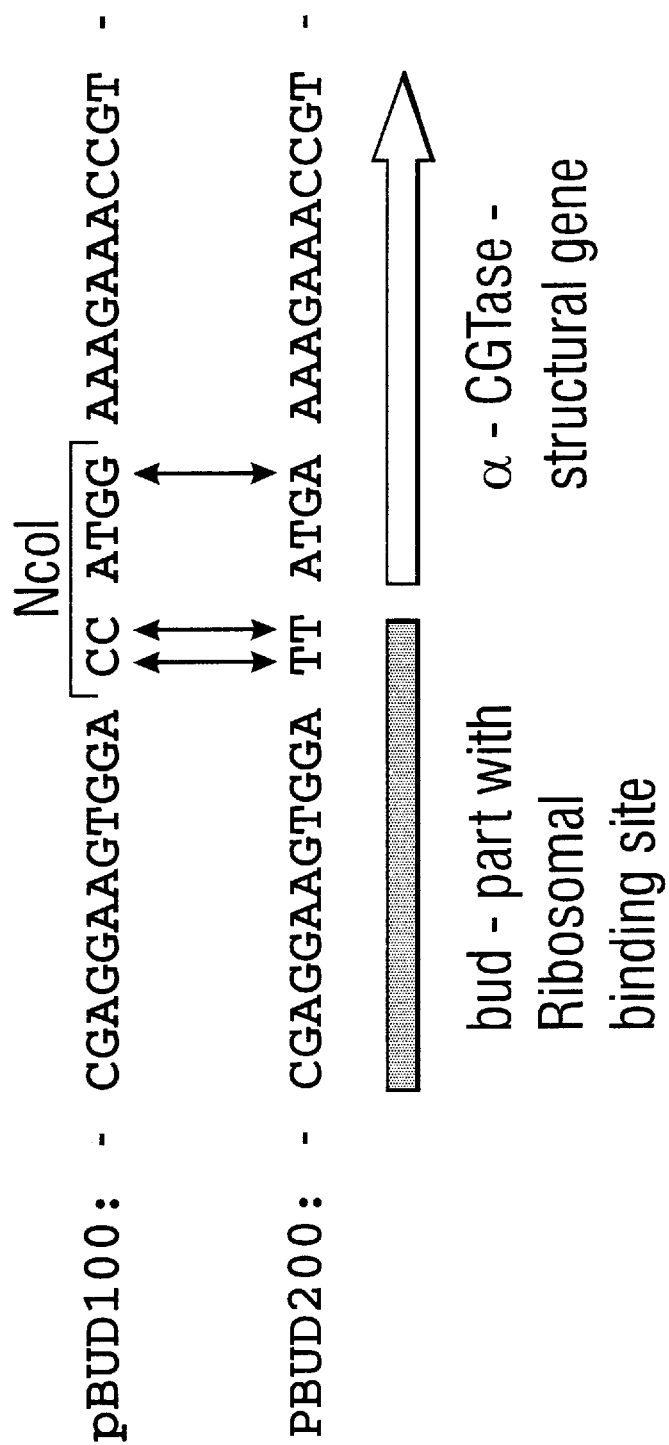
FIG. 10 shows the nucleotide sequence at the bud DNA-CGTase-structional gene junction before (pBUD100; SEQ ID NO:5) and after (pBUD200; SEQ ID NO:6) site-directed mutagenesis.

In order to enable the alpha-CGTase gene on pBUD100 to be translated efficiently, three point mutations were reverted which had been produced during the construction of pBUD100 in order to be able to link the budA promoter and the alpha-CGTase structural gene by way of an NcoI recognition site (FIG. 10).

The DNA sequence in the region of the junction was brought into conformity with the original sequences of budA and alpha-CGTase, respectively, by means of site-directed mutagenesis in accordance with Deng & Nickoloff (1992), *Anal. Biochem.* Vol. 200, pp. 81 et seq. using Oligo9 (Table 1) as the mutagenesis oligo. The positions of the mutagenized bases are shown in FIG. 10 (SEQ ID NO:5 and SEQ ID NO:6). The mutagenized plasmid is designated pBUD200.

EXAMPLE 18

Enzyme test for determining alpha-CGTase activity

The activities of CGTases were determined using the method described by Candussio et al. in *Eur. J. Biochem.* (1990) 191, pp. 177–185.

In each case, 2 units of a CGTase to be tested, per gram of starch, were incubated, at 45° C. for a defined time, with a 5% (w/v) strength solution of a soluble starch (Merck, Darmstadt) in a buffer consisting of 20 mM tris/HC1, pH 7.2, and 5 mM $CaCl_2$. The reaction was subsequently terminated by adding 1.5 parts by volume of methanol. Residual starch whichhad not been reacted was precipitated by incubating for one hour at 4° C. and separated off by centrifugation (10 min, 12000×g). The products which had been formed were determined by means of HPLC on a NUCLEOSIL® 10-NH2 column (Macherey & Nagel, D üren), with defined cyclodextrins (WackerChemie, Munich) being used as a standard.

EXAMPLE 19

Expression of alpha-CGTase by the bud regulator/promoter system on plasmid pBUD200 in *E. coli* WCM105

In order to obtain a production of alpha-CGTase which it was possible to regulate with oxygen, pH and/or acetate, the expression plasmid pBUD200, described in EXAMPLE 16, was transformed into a secretory strain of *E. coli*. *E. coli* WCM105 was used as the *E. coli* secretory strain. This strain was prepared from *E. coli* DS410, as described in EP 338410.

In order to demonstrate regulatable alpha-CGTase production, *E. coil* WCM105/pBUD200 was cultured at 37° C. in potassium phosphate-buffered complete medium (TGYEP at pH 6.5 or pH 8.0); Begg et al. (1977), *FEMS Microbiol. Lett.* Vol. 2, pp. 47–50) to which 0.4% glucose (w/v) and, where appropriate, 40 mM sodium acetate had been added. Anaerobic cultivation took place in serum bottles using the technique of Balch and Wolfe (1976). At an OD600 of between 0.8 and 1.0, the cells were separated off by centrifuging at 5000×g. The cell-free culture supernatant was used, as described in EXAMPLE 15, for determining the alpha-CGTase activity which was contained in it. The results are summarized in Table 12:

TABLE 12

Alpha-CGTase activity in the *E. coli* WCM105/pBUD200 supernatant
(The values which are given are in each case the average from two parallel experimental samples)

| $pO_2$ | pH | Acetate (mM) | CGTase activity (mU/100 ml) |
|---|---|---|---|
| aerobic | 6.5 | 0 | 2.5 |
| anaerobic | 6.5 | 0 | 30.0 |
| anaerobic | 6.5 | 40 | 64.0 |
| aerobic | 8.0 | 0 | <1.0 |
| anaerobic | 8.0 | 0 | 24.0 |
| anaerobic | 8.0 | 40 | 46.5 |

While several embodiments of the present invention have been shown and described, it is to be understood that many changes and modifications may be made thereunto without departing from the spirit and scope of the invention as defined in the appended claims.

---

What is claimed is:

1. An expression system for expression of recombinant proteins which is regulated by acetate, pH and oxygen, which expression system comprises a trans-acting regulator protein, which brings about optimal activation of a 2,3-butanediol (bud) promoter from *Klebsiella terrigena* (DSM2687) in association with oxygen limitation $pO_2$ of 0–5% and in the presence of acetate at 40–60mM concentration and at a pH of a culture medium from pH 6.0 to pH 6.5 and which is encoded by the amino acid sequence of SEQ ID NO:1; and a promoter which is regulated by said regulator protein and which comprises bases 315 to 397 of the DNA sequence of SEQ ID NO:2.

2. A microorganism which harbors at least one expression system as claimed in claim 1.

3. A fermentation process for producing proteins by means of a microorganism, which process comprises providing the microorganism as claimed in claim 2; and utilizing said microorganism in a fermentation process.

4. A process for preparing a microorganism comprising introducing at least one gene for a regulator protein and at least one promoter as claimed in claim 1 into any desired microorganism.

5. Process for preparing a microorganism comprising introducing an expression system of claim 1 into an Fnr-negative microorganism.

6. A purified regulator protein which brings about optimal activation of a 2,3-butanediol (bud) promotor from *Klebsiella terrigena* (DSM2687) in association with oxygen limitation and in the presence of acetate and at a pH of a culture medium of from pH 6.0 to pH 6.5 and which is encoded by the amino acid sequence of SEQ ID NO:1.

7. An isolated gene which encodes the regulator protein as claimed in claim 6.

8. An expression cassette, comprising a promoter which is regulated by the regulator protein of claim 6; said promoter being functionally linked to a structural gene of a heterologous protein which is to be expressed.

9. A microorganism which harbors at least one expression cassette as claimed in claim 8.

10. A fermentation process for producing proteins by means of a microorganism, which process comprises providing the microorganism as claimed in claim 9; and utilizing said microorganism in a fermentation process.

11. A process for preparing a microorganism comprising introducing at least one expression cassette as claimed in claim 8 into any desired microorganism.

12. A process for preparing a microorganism comprising introducing at least one gene for a regulator protein as claimed in claim 6, into any desired microorganism.

* * * * *